United States Patent [19]
Ryan

[11] Patent Number: 5,954,696
[45] Date of Patent: Sep. 21, 1999

[54] PRESSURE INFUSION PUMP

[75] Inventor: Timothy C. Ryan, Laguna Hills, Calif.

[73] Assignee: B. Braun Medical, Inc., Bethlehem, Pa.

[21] Appl. No.: 08/990,362

[22] Filed: Dec. 15, 1997

[51] Int. Cl.⁶ .................................................. A61M 5/142
[52] U.S. Cl. ................................... 604/141; 128/DIG. 12
[58] Field of Search ................................... 604/131, 140, 604/141; 128/DIG. 12

[56] References Cited

U.S. PATENT DOCUMENTS

| | | | |
|---|---|---|---|
| D. 287,277 | 12/1986 | Kosako et al. | D24/17 |
| D. 348,730 | 7/1994 | Walker et al. | D24/111 |
| 3,153,414 | 10/1964 | Beall et al. | 128/214 |
| 3,507,278 | 4/1970 | Werding | 128/214 |
| 3,625,401 | 12/1971 | Terry | 222/103 |
| 3,640,277 | 2/1972 | Aelberg | 128/214 F |
| 3,895,741 | 7/1975 | Nugent | 222/103 |
| 4,043,332 | 8/1977 | Metcalf | 128/214 E |
| 4,237,881 | 12/1980 | Beigler et al. | 128/214 F |
| 4,430,078 | 2/1984 | Sprague | 604/141 |
| 4,613,327 | 9/1986 | Tegrarian et al. | 128/DIG. 12 |
| 4,626,243 | 12/1986 | Singh et al. | 604/141 |
| 4,673,392 | 6/1987 | Keime | 604/141 |
| 4,684,367 | 8/1987 | Schaffer et al. | 604/140 |
| 4,735,613 | 4/1988 | Bellin | 604/141 |
| 4,784,652 | 11/1988 | Wikstrom | 604/141 |
| 5,045,064 | 9/1991 | Idriss | 604/132 |
| 5,059,182 | 10/1991 | Laing | 604/142 |
| 5,088,983 | 2/1992 | Burke | 604/141 |
| 5,106,374 | 4/1992 | Apperson et al. | 604/140 |
| 5,135,499 | 8/1992 | Tafani et al. | 604/141 |
| 5,163,909 | 11/1992 | Stewart | 604/140 |
| 5,176,644 | 1/1993 | Srisathapat et al. | 604/141 |
| 5,207,645 | 5/1993 | Ross et al. | 604/141 |
| 5,219,327 | 6/1993 | Okada et al. | 128/DIG. 12 |
| 5,308,335 | 5/1994 | Ross et al. | 604/141 |
| 5,348,539 | 9/1994 | Hersskowitz | 604/141 |
| 5,364,364 | 11/1994 | Kasvikis et al. | 604/131 |
| 5,382,236 | 1/1995 | Otto et al. | 604/141 |
| 5,398,850 | 3/1995 | Sancoff et al. | 222/386.5 |
| 5,423,759 | 6/1995 | Campbell | 128/DIG. 12 |
| 5,433,704 | 7/1995 | Ross et al. | 604/67 |
| 5,492,534 | 2/1996 | Athayde et al. | 604/141 |
| 5,554,123 | 9/1996 | Herskowitz | 604/141 |

*Primary Examiner*—Paul J. Hirsch
*Attorney, Agent, or Firm*—Christie, Parker & Hale, LLP

[57] ABSTRACT

A portable, ambulatory infusion pump for use with standard pre-filled infusion medicament containers is powered by a miniature compressed gas cylinder coupled to a mechanical pressure regulator which supplies regulated gas at a substantially constant pressure to an inflatable bladder. The bladder is positioned between a substantially rigid pressure surface and a moveable pressure transfer plate and pushes against the transfer plate when inflated. A pre-filled medicament container is positioned over the pressure transfer plate and is squeezed between the transfer plate and the pump housing cover as the plate is displaced in response to inflation of the flexible bladder. A safety interlock assembly is connected between the pressure regulator and the inflatable bladder and prevents inflation of the bladder unless the housing cover is completely closed. Upon inadvertent opening of the pump, the internal pressurization system is vented to atmosphere.

19 Claims, 6 Drawing Sheets

PRESSURE INFUSION PUMP

FIELD OF THE INVENTION

The present invention is directed, generally, to an ambulatory drug infusion pump for administering antibiotics, antivirals and other IV medications for critically ill patients and for home care or out-patient applications. More particularly, the invention relates to an ambulatory infusion pump powered by a renewable $CO_2$ pressurized gas source and adapted for use with prepackaged, disposable, standard medical containers.

BACKGROUND OF THE INVENTION

Over the years, infusion pumps have been used to deliver a wide variety of medication types and fluids, intravenously, to medical patients. Infusion pumps used to deliver intravenous fluids and solutions for a wide variety of medical therapies including chemotherapy, antiviral and antibiotic therapy, and also include intravenous introduction of blood, saline solutions, glucose solutions and various other solutions comprising pharmaceuticals.

In many situations, a patient may require multiple daily therapies, intermittent infusion, or a slow and continuous introduction of medicament liquid into the patient's system. Moreover, certain therapies require medicament liquid or pharmaceutical solutions to be infused over a particular period of time which may range anywhere from about 30 minutes to about several hours, for a therapeutic dose. It is therefore very important that these medicament liquid or pharmaceutical solution doses be administered completely and with a highly accurate introduction rate (flow rate).

Currently, a variety of devices exist that are able to deliver medicament liquids and pharmaceutical solutions intravenously to a patient. In the past few years, certain of these devices have offered some degree or portability, but the most widely utilized of these devices typically require a patient to be confined to a bed, thus limiting the options available for patients who are able to be ambulatory.

So called ambulatory infusion pumps are gaining currency in medical technology, given the trend towards shorter hospital stays and increasing reliance on out-patient and home care treatment. Such ambulatory devices typically function on an infusion pump delivery principle which pumps a medicament liquid or other IV solution into the patient. The pressure developed by the infusion pump is designed to overcome the resistance of the patient's internal pressure and include regulators or restrictors in the IV tubing set to attempt to control the rate of flow of the IV solution into the patient.

The prior art discloses several types of ambulatory infusion pumps which attempt to approximate reasonable levels of accuracy in administering IV solutions. For example, it is common to pressurize a container filled with a medicament liquid or IV solution by transmitting a hydrostatic or gas pressure developed in an external or internal gas-filled bladder to the IV solution container. By maintaining a constant pressure in the bladder, it was hoped that the bladder would exert (transmit) a constant pressure to the IV solution container, thereby developing a constant flow rate of medicament liquid at the point of infusion. However, as is well understood in the art, the gas pressure inside an expanding bladder necessarily decreases as the bladder's internal volume increases, in accordance with Boyle's Law.

In order to obtain some measure of accuracy and control in IV solution delivery, the various infusion pump systems that generate their own pressure to overcome patient pressure resistance must contain some means for controlling a fluid flow rate at the various pressures and flow rates required by multiple therapeutic applications. Common stationary gravity feed units provide some limited control possibilities by adjusting the height of a medical container above the point of infusion, but this technique requires additional apparatus upon which to hang a medical container, thus limiting the unit's portability. Certain electromechanical infusion pumps, such as volumetric peristaltic or piston-cylinder pumps provide for relatively accurate delivery, but have rather large power requirements which necessitates frequent battery replacement.

In the more common elastomeric-type infusion pump devices, the elastomeric pumps use the pressure of an expanding elastomeric element to push an IV solution through a rate controlling orifice or a constrictive clamp. While relatively simple, this technique is only useful to provide a constant flow rate if the pressure head of the liquid entering the rate controlling orifice is generally constant. As soon as the pressure varies, the IV solution flow rate will necessarily change in response.

In addition to these disadvantages, contemporary ambulatory infusion pumps also require IV solutions or medicament liquids to be hosted in special containers which are not necessarily adapted to the use of standard, pre-filled single dose IV solution containers. Where contemporary infusion pumps are not able to be used with a standard IV solution container, the medicament liquid desired to be infused must be separately compounded and then introduced into the specialized infusion pump container. This practice, of course, has implications for the sterility of the medicament solution since the solution must pass through additional handling steps in the preparation and transfer process, prior to being introduced to a patient. The requirement to compound and transfer the IV solution is time consuming and increases the risk of contamination.

Further, in order to minimize the various disadvantageous features of conventional ambulatory infusion pumps, certain prior art-type devices have incorporated additional systems, at a substantial penalty and complexity and added cost, to address variable flow rates and non uniform pumping pressures. For example, U.S. Pat. No. 5,348,539 discloses an infusion pump with an inflatable chamber, terminated in a diaphragm which expands and contracts under fluid pressure in order to compress the sidewalls of an IV solution container. A fluid, in the form of a liquid, is transferred to and from the inflatable chamber through a reservoir. The system includes a complex valve arrangement by which the fluid is introduced into the chamber and withdrawn therefrom. The overall system is controlled by a electronic circuitry which includes pressure sensors in the inflatable chamber and logic circuitry which controls a reversible fluid pump which moves the liquid between the reservoir and the inflatable chamber, the whole monitored and controlled by a suitable micro-controller IC chip. While relatively compact and accurate, this system is also highly complex, expensive and requires a great deal of electrical power to operate.

An additional prior art-type system is disclosed by U.S. Pat. No. 5,106,374 in which gas pressure uniformity is addressed by providing a housing with a series of cavities in which there are provided expandable pressure regulator tubes. The regulator tubes are interconnected through a series of passageways, connectors, etc. to an inflatable, flexible, substantially non-stretchable diaphragm provided in yet another housing cavity. The diaphragm provides the pressure source against an IV solution container with the expandable pressure regulator tubes defining a pressure reservoir. The system becomes charged when the regulator tubes are expanded by a, for example, compressed gas source. Once the infusion process is initiated, the regulator tubes gradually deflate forcing the non-expandable diaphragm against a flexible IV solution container. Medicament is infused at a substantially steady rate into the patient until the medicament bag has been emptied. While again rather compact and reasonably accurate, this particular system is disadvantageous in terms of component complexity and lack of flexibility.

Accordingly, while various systems are known for providing intravenous delivery of fluids to an ambulatory patient, there is no single system that is reusable, is able to be used with standard IV solution containers as opposed to specialized disposables, is simple to operate, includes a minimum of component parts, requires no source of electrical energy, and is able to store and deliver anywhere from about 50 to about 250 mL of medication using standard manufacturers' flexible drug containers, at flow rates of from about 50 mL to about 200 mL per hour.

BRIEF DESCRIPTION OF THE DRAWINGS

These and other features, aspects, and advantages of the present invention will be more fully understood when considered with respect to the following detailed description, appended claims, and accompanying drawings wherein:

FIG. 1c is a semi-schematic simplified front view of the ambulatory infusion pump of FIG. 1a;

FIG. 1d is a semi-schematic simplified bottom plan view of the ambulatory infusion pump of FIG. 1a;

DETAILED DESCRIPTION OF THE INVENTION

Figure 1A:
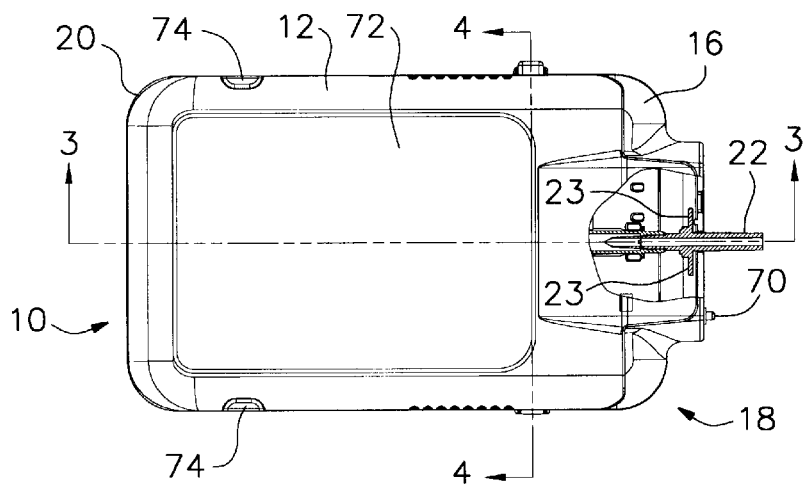
FIG. 1a is a semi-schematic simplified top plan view of an ambulatory infusion pump in accordance with practice of principles of the invention.
Figure 1B:
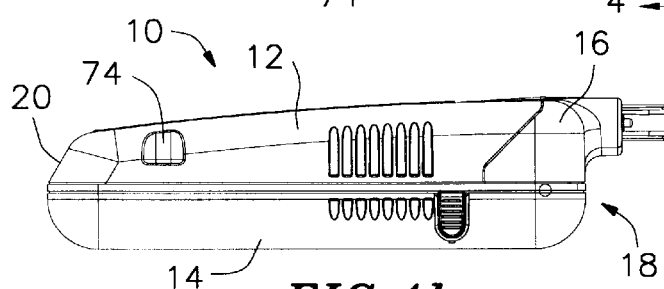
FIG. 1b is a semi-schematic simplified side view of the right side, from the perspective of FIG. 1a, of an ambulatory infusion pump in accordance with practice of principles of the invention.

Referring now to the drawings, a simple, low cost ambulatory infusion pump according to the invention is illustrated in top plan view, side view, front end view and bottom plan view, respectively, in FIGS. 1a, 1b, 1c and 1d. Since each of the views depicted in FIGS. 1a–1d contains common elements, as well as for ease in following the description, like components, represented on each of the views, will be identified with the same reference numeral throughout the specification.

One embodiment of an ambulatory infusion pump in accordance with the present invention is constructed of a multiple-part housing, generally indicated at 10 and including a top housing portion, or cover, 12, a bottom housing portion, or base, 14, and a front or end piece 16, which, when mated together, in combination define an enclosure for containing a standard IV solution container and for supporting and containing various components for infusing a medicament solution to a patient on a controlled basis. The infusion pump housing 10 is generally rectangular in shape and measures about 2 inches in thickness, 4 inches in width and 6 inches in length. Although described as generally rectangular, it may be seen from the illustrations of FIGS. 1a–1d that the infusion pump housing 10 has rounded corners and edges and tapers slightly from a maximum thickness at a first end 18, generally taken to be the front end, to a minimum thickness at a second end 20, termed herein the back end. While also making for an aesthetically pleasing appearance, tapering the housing functionally allows for providing a region of maximum thickness within which to position relatively bulky internal components, as will be described in greater detail below, while at the same time maintaining the internal volume of the infusion pump as low as possible in order to realize a more gas efficient design. It will, of course, be evident to those having skill in the art, that internal volumetric efficiency may be improved by molding the housing 10 into an exterior shape which conforms completely to the interior volumetric surfaces of the pump's internal components such that there is little to no interior "dead" space. Such a more compact and streamlined design would, of course, pay some slight penalty in increased cost of manufacture, while obtaining some slight benefit in gas efficiency.

As illustrated in FIGS. 1a–1d, the infusion pump housing 10 is manufactured of a high impact plastic, such as ABS, which may be injection molded, pressure formed, or the like and is sized and shaped to be easily manipulated and accessed by patients who may be infirm or otherwise unable to manipulate either heavy or bulky devices. As can be seen in the illustrations of FIGS. 1a–1d, the front portion 18 of the housing is configured to receive a standard drug spike 22 which is inserted into and protrudes through a slot 24 provided in the end piece 16 for such purpose. The drug spike 22 is a typical commercially available apparatus, such as may be found included with a variety of IV set configurations, such as the METRISET and ADDitIV series of administration sets, manufactured and sold by McGaw, Inc. of Irvine, Calif. The spike 22 is designed and adapted to be inserted into a standard set port or spike port of a conventional IV solution container.

Figure 1C:
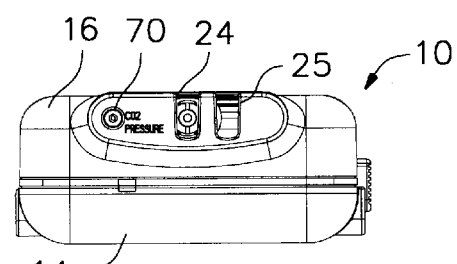
Figure 1D:
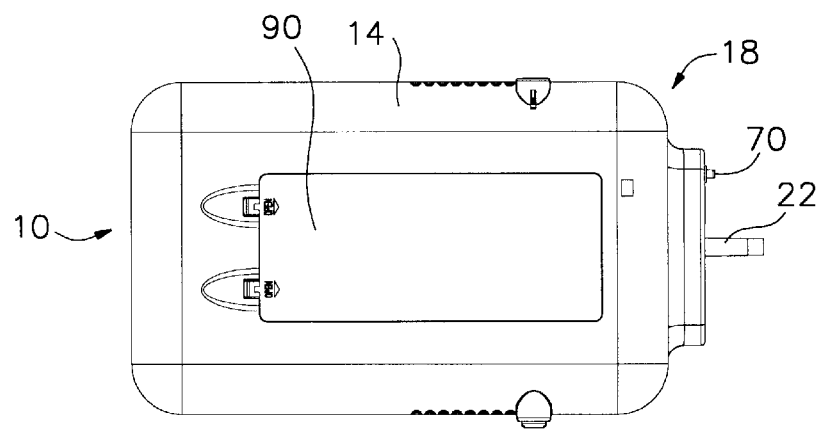

In FIG. 1a, it can be seen that the spike 22 is retained in place by the spike slot (24 of FIG. 1c). The spike 22 includes longitudinal flanges 23 which bear against the inside surface of the end piece 16, to either side of the spike slot 24, such that once the spiked medical container is disposed within the pump, and the cover closed, the spike cannot be inadvertently withdrawn from the pump and, thus, the spike port of the container.

In practice, any one of a number of standard IV solution containers may be used with the infusion pump of the present invention, but either 50 mL, 100 mL or 250 mL standard flexible solution containers are preferred. The spike end of the drug spike 22 is inserted into the container's set or spike port and the assembled, spiked, IV solution container is inserted into the infusion pump in a manner to be described further below. It will, of course, be understood that the opposite end of the spike will be coupled in combination with an administration set, which may include a check valve, in order that solution integrity is maintained in the administration container prior to operation of the pump.

The front end 16 of the pump includes an additional slot 25, disposed adjacent the spike slot 24, and comprising a similar sized opening. The additional slot 25 is provided so that dual-ported containers may be used by the pump without requiring undue manipulation of the housing by a patient. An admixture drug may be introduced into the container, prior to infusion, by accessing such a container's "drug" port with a spiked drug vial, for example, through the second access slot 25. In such a situation, the administration spike may remain attached to the container's primary port. Admixture or reconstitution, thus, does not require disconnecting and reconnecting various spikes and is, therefore, more efficient and less likely to lead to improper dosages and/or a potentially harmful drug bolus developed in the container.

Figure 2:
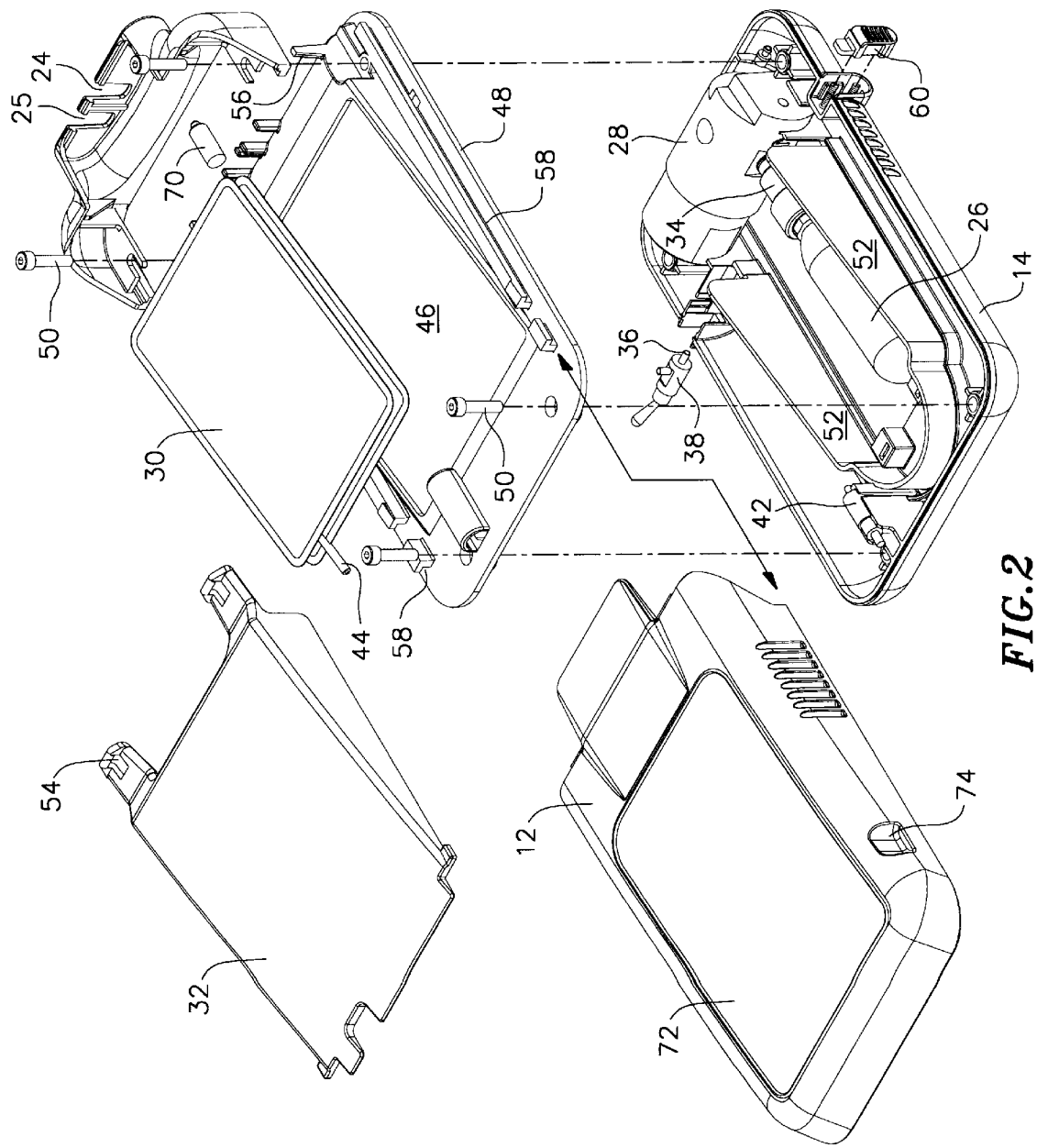
FIG. 2 is a semi-schematic exploded, perspective view of one embodiment of an ambulatory infusion pump in accordance with the invention.

Turning now to FIG. 2, there is depicted a perspective, exploded view of an exemplary embodiment of an infusion pump according to the present invention which illustrates the internal construction of the pump and its internal components. As shown in FIG. 2, the housing's bottom portion 14 is dish shaped and defines a mounting base for a simple, non-electrical, reusable ambulatory pump unit.

The pump unit suitably comprises a gas source in the form of a miniature $CO_2$ cylinder 26 coupled to deliver gas under pressure through a pressure regulator 28 to thereby inflate a flexible bladder 30 which acts upon a pivotally mounted pressure transfer plate 32 in such a manner that a filled IV solution container (best seen in FIG. 6) is squeezed between the pressure transfer plate 32 and the inside surface of the upper housing portion 12 thus placing the container's contents under pressure and forcing the IV solution out through the drug spike 22, thereby administering the infusion.

In particular, the miniature $CO_2$ cylinder 26 is preferably one of the type which is commonly used as a propellant source for pellet guns, commercial life jackets and life vests, motorcycle tire inflation kits, and the like. Miniature $CO_2$ cylinders of this type are commonly configured to contain from about 8 to about 16 grams of $CO_2$ gas at an internal cylinder pressure of approximately 500 to 1000 psi depending on the ambient temperature, and nominally about 850 psi. The cylinders may be threaded or non-threaded, depending on the configuration of the matching collar or bushing, and are commercially available from, for example, Leland Limited, Inc. of Bedminster, N.J., in a variety of standard forms. Preferably the miniature $CO_2$ canister 26 is a Leland 82122, MIL-C-601G, threaded $CO_2$ cylinder.

The $CO_2$ cylinder 26 is connected to and mates with a threaded puncture bushing 34 which is, in turn, coupled to and forms the input port of a mechanical pressure regulator 28. The pressure regulator 28 functions to regulate the cylinder pressure of the $CO_2$ gas and deliver the gas at an outlet pressure in the range of from about 3 to about 25 psi during operation of the device.

The pressure regulator 28 is likewise a commercially available pressure regulator. Suitable such regulators are manufactured and sold by Leland Limited, Inc. of Bedminster, N.J. and a variety of other vendors. However, in choosing a suitable pressure regulator, as well as in designing the remainder of the pressurization system, care should be taken such that the maximum occlusion pressure safety limits of ANSI/AAMI ID 26-1992 are not exceeded. Briefly, the ANSI standard requires that an infusion pump designed in accordance with the maximum occlusion pressure specifications should not be capable of developing a system pressure which exceeds 45 psig when evaluated at the distal end of the IV administration set. The standard also requires that the pressurized gas system include a pressure relief valve operative at the 45 psi trip point.

Accordingly, the outlet pressure of the pressure regulator device 28 must be carefully chosen such that the maximum outlet pressure, in combination with the developed hydrostatic pressure within an IV solution container, does not exceed 45 psig at the point of infusion.

Regulated, low-pressure $CO_2$ gas (at an outlet pressure of from about 3 to about 10 psi) is ducted from an outlet port of the pressure regulator 28 to an inlet port 36 of a single-throw, lever-operated on/off switch 38, through, for example, flexible tubing of a type suitable for passing gasses at the noted pressures. Switch 38 functions as a directional port such that when the switch is in the off position, low-pressure $CO_2$ gas is prevented from moving further through the system. When the switch 38 is in the on position, a direct pass-through port is opened and the $CO_2$ gas is allowed to proceed through the switch.

A housing, or shroud, may also be mounted over the actuating lever of the switch and configured such that the lever cannot be moved to the on position unless the pump's housing components are fully assembled. This would prevent inadvertent operation of the on/off switch causing loss of $CO_2$ to the ambient atmosphere. As an additional safety feature, after the on/off switch 38 is properly activated, the $CO_2$ gas flow path is coupled by flexible tubing to the inlet port of a safety switch 42 which functions to safely shut-off the low-pressure $CO_2$ gas supply to the remainder of the system when the housing cover 12 is not in a fully closed position and further functions to vent any $CO_2$ gas, already pressurizing the bladder 30, to atmosphere.

If cover 12 is fully closed, the safety switch 42 allows compressed $CO_2$ gas to pass therethrough to a fill port 44 which communicates with the interior of a flexible, urethane plastic bladder 30 which rests on a substantially flat, rigid pressure surface 46 provided on an intermediate pressure member 48 which spans the housing bottom portion 14 and which is affixed thereto. The pressure member may be attached to the housing bottom 14 by any of a variety of conventional fasteners, such as push-pins, screws, snap-fit posts and detents, and the like. In the illustrated embodiment of FIG. 2, simple, mechanical fasteners 50 are preferred.

The pressure surface 46 is inclined, slightly, in the direction of the housing's maximum thickness, so as to describe a ramp with respect to the major plane of the internal pressure member 48. The pressure surface is prevented from deforming in a downward direction, as a result of pressure exerted by the bladder 30, by a pair of laterally spaced-apart inclined support rails 52 provided in the housing bottom portion 14 for such purpose. The angle described by the spaced-apart rails 52 is substantially the same as the angle described by the pressure surface with respect to the major plane of the intermediate pressure member and are configured such that the pressure surface rests on the upper edge of the spaced-apart rails 52 when the intermediate pressure member 48 is affixed to the housing bottom portion 14. Pressure developed against the pressure surface 46 by expansion of the urethane bladder 30 will not cause the pressure surface to deform vertically downwardly in a manner to relieve internal pressure in the bladder. The rails 52, in combination with the pressure surface 46 and the housing bottom 14 also function to define an interior volume in which the $CO_2$ gas cylinder is contained. The rails are spaced-apart a sufficient distance so that an additional, "refill" $CO_2$ cylinder may be provided within the pump enclosure, along side the cylinder providing motive power to the pump.

An upper pressure plate 32 is disposed over the top surface of the bladder 30 such that the bladder is sandwiched between the upper pressure plate 32 and the pressure surface 46. Upper pressure plate 32 is connected to the infusion pump housing end piece 16 by elongate generally L-shaped tabs 54, which extend from an end of the upper pressure plate, and which engage mating receptacles or slots 56 in the housing end piece 16. The tabs 54 and mating receptacles 56, in combination, allow the upper pressure plate 32 to pivot about an axis in the region of the tabs 54 and slots 56.

Figure 3:
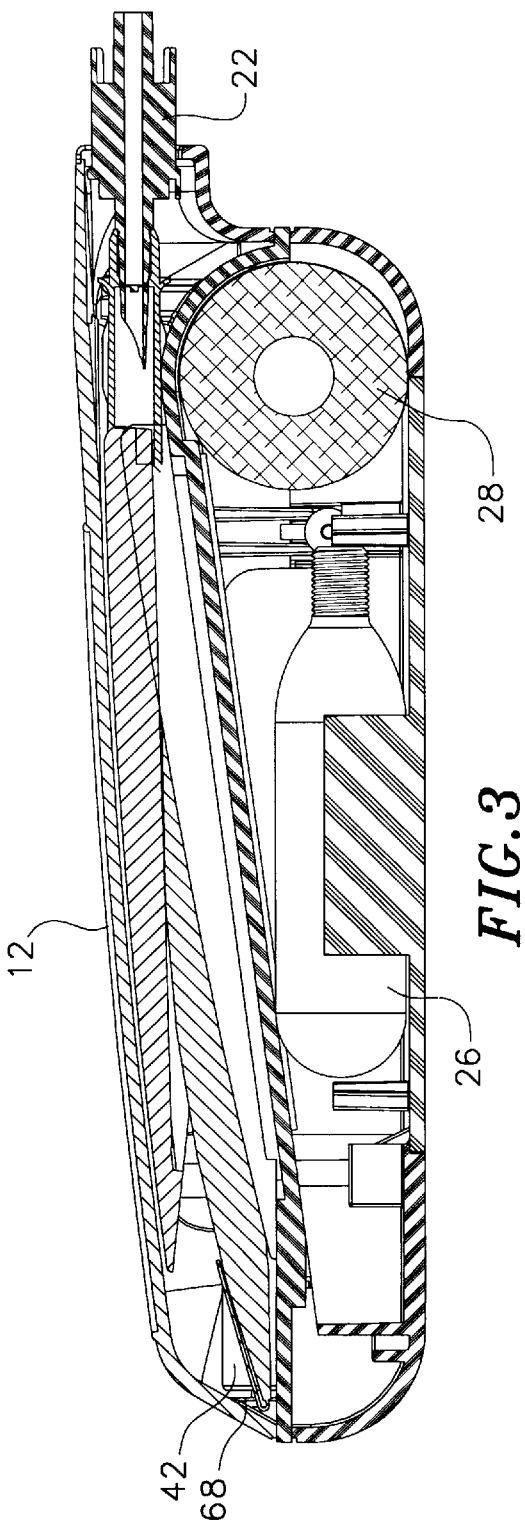
FIG. 3 is a semi-schematic cross-sectional side view of the ambulatory infusion pump of FIG. 2.

Accordingly, when compressed $CO_2$ gas is introduced into the flexible bladder 30 and the bladder expands in response thereto, the volumetric expansion of the bladder causes the upper pressure plate 32 to pivot such that its major upper surface is forced into a position adjacent the major upper surface of the housing's top portion 12 (best seen in FIG. 3).

It will be understood that were an IV solution container to be disposed between the upper pressure plate 32 and the housing top portion 12, volumetric expansion of the bladder will cause the upper pressure plate 32 to transfer the pressure developed within the bladder to the IV solution container. The pressure surface 46, supported by the spaced-apart rails 52 forms a substantially non-deformable base plate to the bladder 30, such that all pressure developed within the bladder is transferred to the movable upper pressure plate 32 and thence to the IV solution container.

In its assembled form, the flexible bladder 30 is disposed on the pressure surface 46 of the internal pressure member 48 and the internal pressure member assembly is affixed into the housing bottom portion 14 so as to cover the $CO_2$ cylinder 26, pressure regulator 28 and the flexible coupling hoses, and secured into place by, for example, snap-fit or friction-fit pins 50. The upper pressure plate 32 is set over the flexible bladder 30 and engaged in place by the housing front portion 16 which is also secured over the front edge of the internal pressure member 48.

Figure 6:
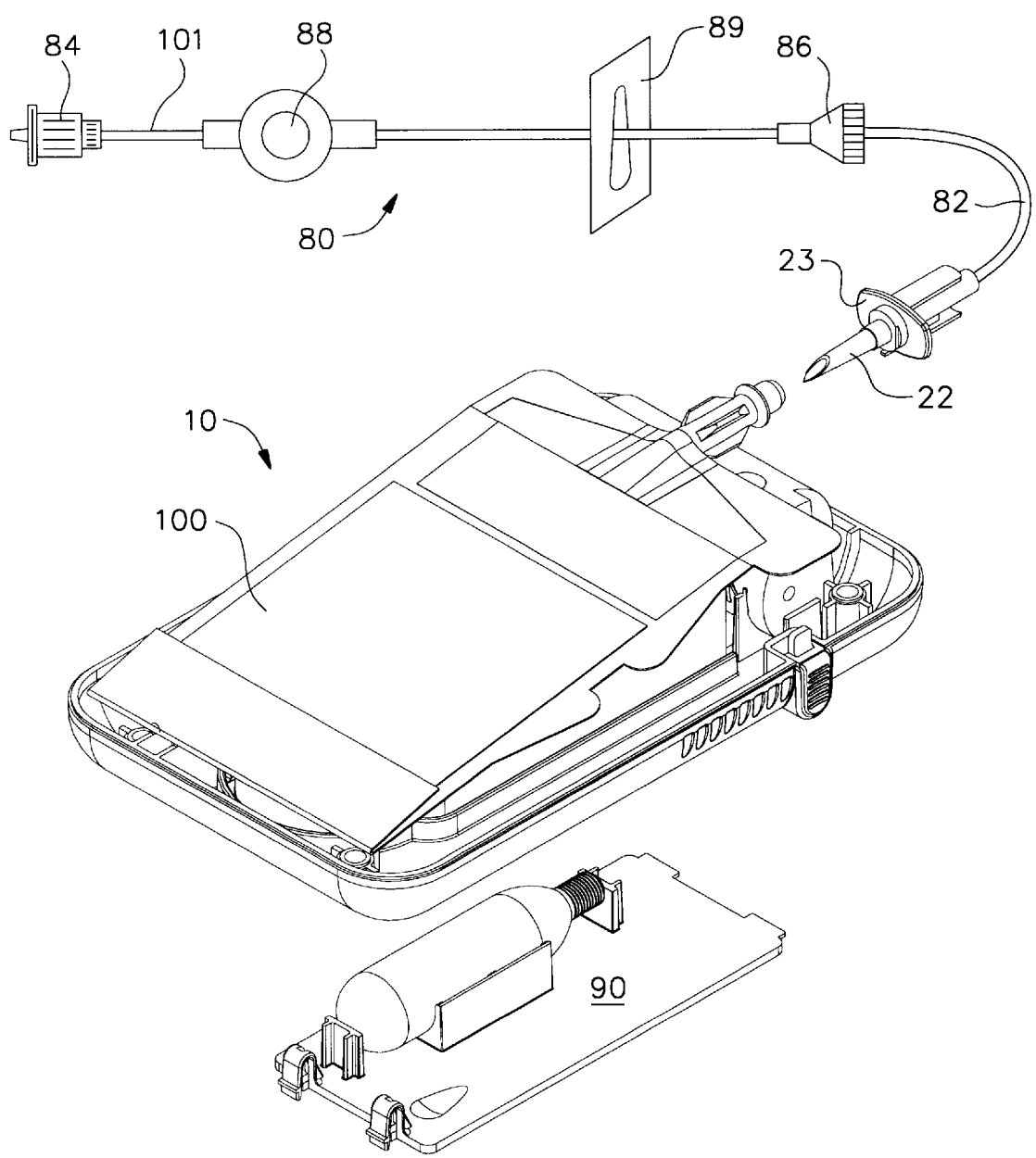
FIG. 6 is a semi-schematic perspective view of an IV infusion set useful for practice of principles of the present invention.

In the embodiment illustrated in the drawings, particularly in connection with the embodiment of FIG. 6, a standard manufacturer's IV solution container 100, such as a PAB container, an EXCEL container, or a DUPLEX container, all manufactured and sold by B.Braun/McGaw, Inc. of Irvine, Calif., is placed on the upper surface of the upper pressure plate 32 and spiked with an IV administration set, to access the medicament liquid contained within. After the container 100 is spiked, the container is placed on the pressure plate 32 such that the spike protrudes through the access slot (24 of FIGS. 1c and 2). The spike is retained in place by locating flanges 23 (best seen in FIGS. 1a and 6) which extend beyond the edges of the locating slot 24 and engage the inside surface of the front edge portion (16 of FIG. 1b) of the housing in order to retain the spiked container in place. The manner in which the spike engages the inside surface of the housing is best illustrated by the cut away portion of FIG. 1a. After the IV container is in position, the upper housing portion 12 (the cover) is closed over the infusion pump, and the apparatus is ready for infusion.

Figure 4:
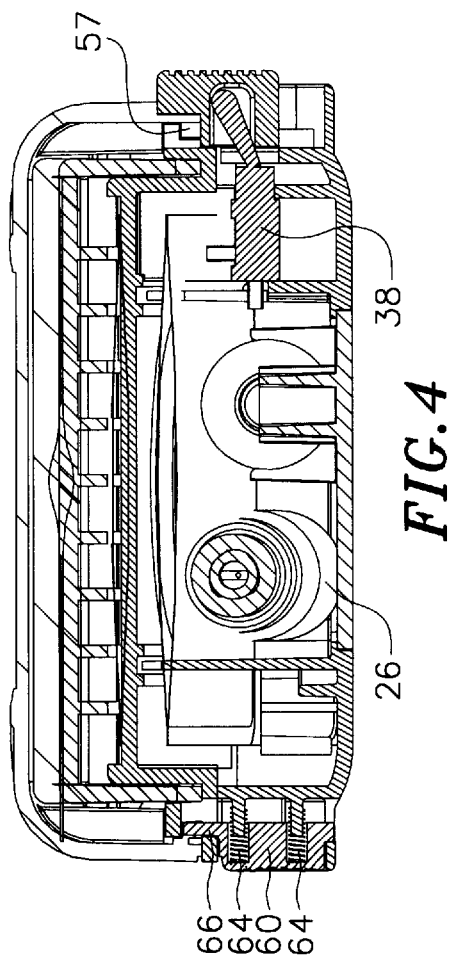
FIG. 4 is a semi-schematic cross-sectional end view of the ambulatory infusion pump of FIG. 2.

As best seen in connection with FIG. 2 and the cross-sectional end view of FIG. 4, as the cover is closed, lateral flanges 57, disposed along the bottom rim of the cover, are engaged into longitudinal slots 58 formed along the upper surface of the pressure surface 46. The cover flanges 57 are first inserted into the slots 58 and the cover is slid lengthwise along the pressure surface 46 the unit is fully closed.

Figure 5:
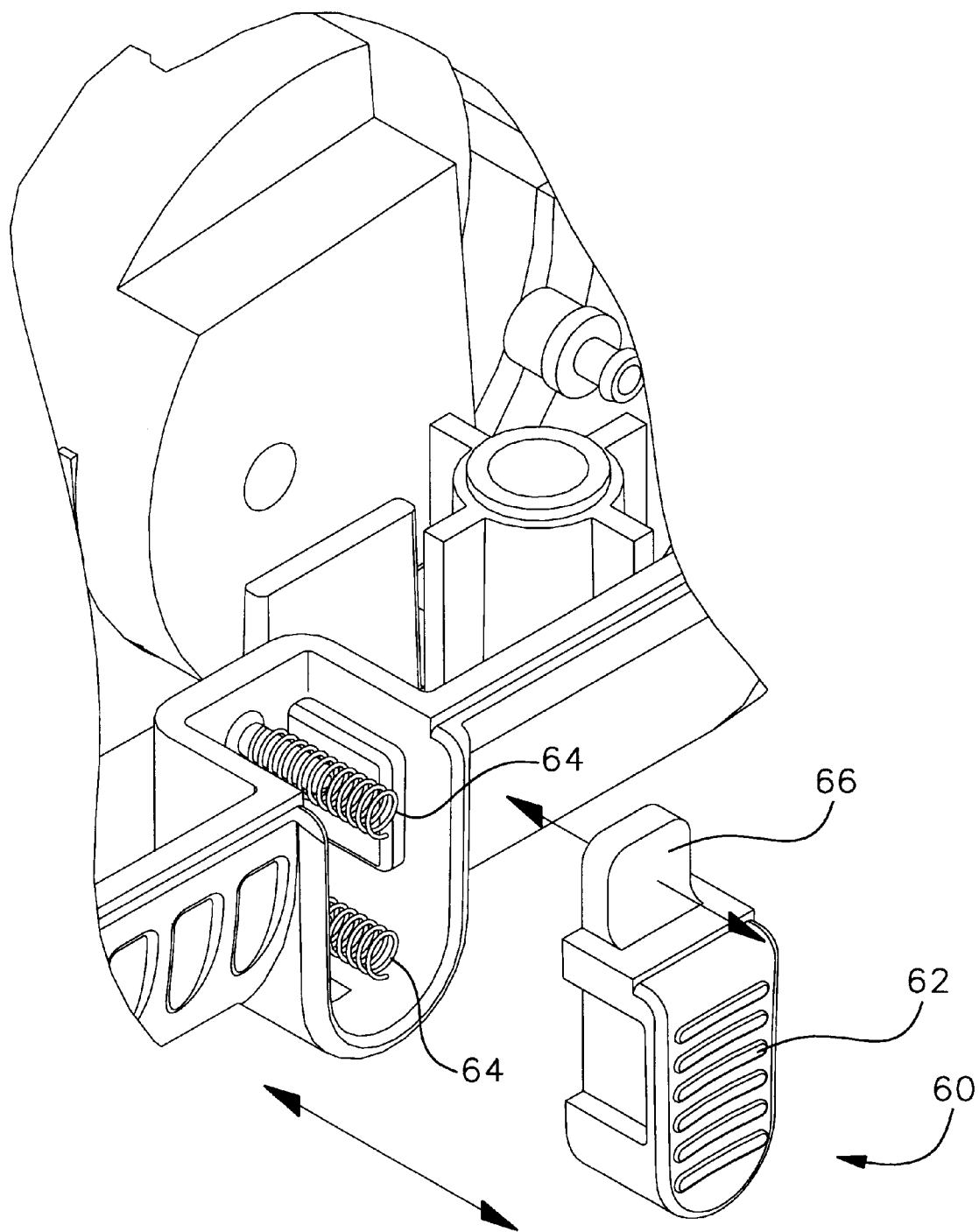
FIG. 5 is an enlarged exploded perspective view of a safety switch in accordance with the invention.

Having reference now to FIG. 2, the enlarged perspective view of a portion of the pump housing of FIG. 5 and the cross-sectional end view of FIG. 4, the cover is advanced along the pressure surface 46 until it engages a cover open/close switch 60. The switch 60 suitably comprises a button 62 mounted in a receptacle at the side of the housing, over a pair of helical springs 64 which are loaded when the button 62 is pushed in the direction of the housing body. A tab 66 is formed on the top of the button 62 and is adapted to be received in a corresponding slot cut into the slide flange of the cover 12. When the button 62 is pushed, the tab 66 is forced inward a sufficient distance to clear the detent slot, allowing the cover to be slid back and forth along the top surface of the pressure surface 46. When the button 62 is released, the helical springs 64 urge the button 62 and the tab 66 away from the housing body such that the tab 66 will detent into the flanges slot to prevent any further forward or backward movement of the cover. The cover is now closed and prevented from further movement by the cover open/close switch 60.

Returning now to FIG. 2 and with reference to the semi-schematic cross-sectional side view of the invention at FIG. 3, closing the housing cover 12 activates a safety interlock switch 42, such that unless the cover is securely in position over the housing bottom portion 14, the safety switch 42 will render the system inactive such that the flexible bladder 30 cannot be pressurized. Were it otherwise, pressurizing the flexible bladder 30 would force the pressure plate 32 against an insecurely fastened cover 12, causing the cover to fly off and resulting in damage to the system, IV solution leakage, and failure of the infusion therapy. The interlock safety switch 42 suitably comprises a piston-type vent valve, activated by a push-pin which protrudes from its distal end in the direction of the back of the cover. As best seen in FIG. 3, the back surface of the cover 12 includes a generally vertical engaging surface 68, positioned to engage the end of the push-pin of the safety valve 42, as the cover is advanced over the housing bottom. When the cover is advanced to the fully closed position, and the cover open/close switch 60 is interposed in the flange slot, the engaging surface 68 has advanced the activation push-pin of the safety interlock switch 42 sufficiently into the switch to close a bleed valve.

Thus, in accordance with the invention, when the safety switch 42 is activated, thereby closing its internal bleed valve, pressurized $CO_2$ gas is directed through the switch 42 to the fill port 44 of the flexible bladder 30. When the safety switch 42 is not activated, i.e., when the cover 12 is not in its fully closed position, its internal bleed valve defaults to an open condition and any pressurized $CO_2$ gas which may be retained in the bladder 30 is vented to the atmosphere. Since the cover is necessarily not in a fully closed position, the on/off switch 38 is prevented from introducing pressurized $CO_2$ gas from the pressure regulator to the distribution system.

Once the infusion pump cover 12 is in its fully closed position, and the safety interlock switch 42 is closed to the atmosphere and opened to the $CO_2$ gas source, infusion is initiated by activating the on/off switch 38. In FIG. 2, and with reference to the semi-schematic cross-sectional end view of FIG. 4, the on/off switch 38 is a lever-operated 2-way valve which is open to the $CO_2$ gas source (the pressure regulator 28) when the lever is in a first (on) position and is open to the atmosphere so as to bleed the line pressure, when the lever is in a second (off) position. When the on/off switch 38 is activated, compressed $CO_2$ gas at an outlet pressure of approximately 3–25 psi is directed through the switch 38 and the interlock safety switch 42 to the flexible bladder 30. The bladder is pressurized and, as it expands, the bladder pushes against the pressure plate 32 which, in turn, transfers pressure to the IV solution container to begin infusion therapy. In the embodiment illustrated, the pressurized system comprising the flexible bladder 30 and the IV solution container will be maintained at a substantially constant pressure of approximately 3–25 psi throughout the operational regime of the device.

Figure 7:
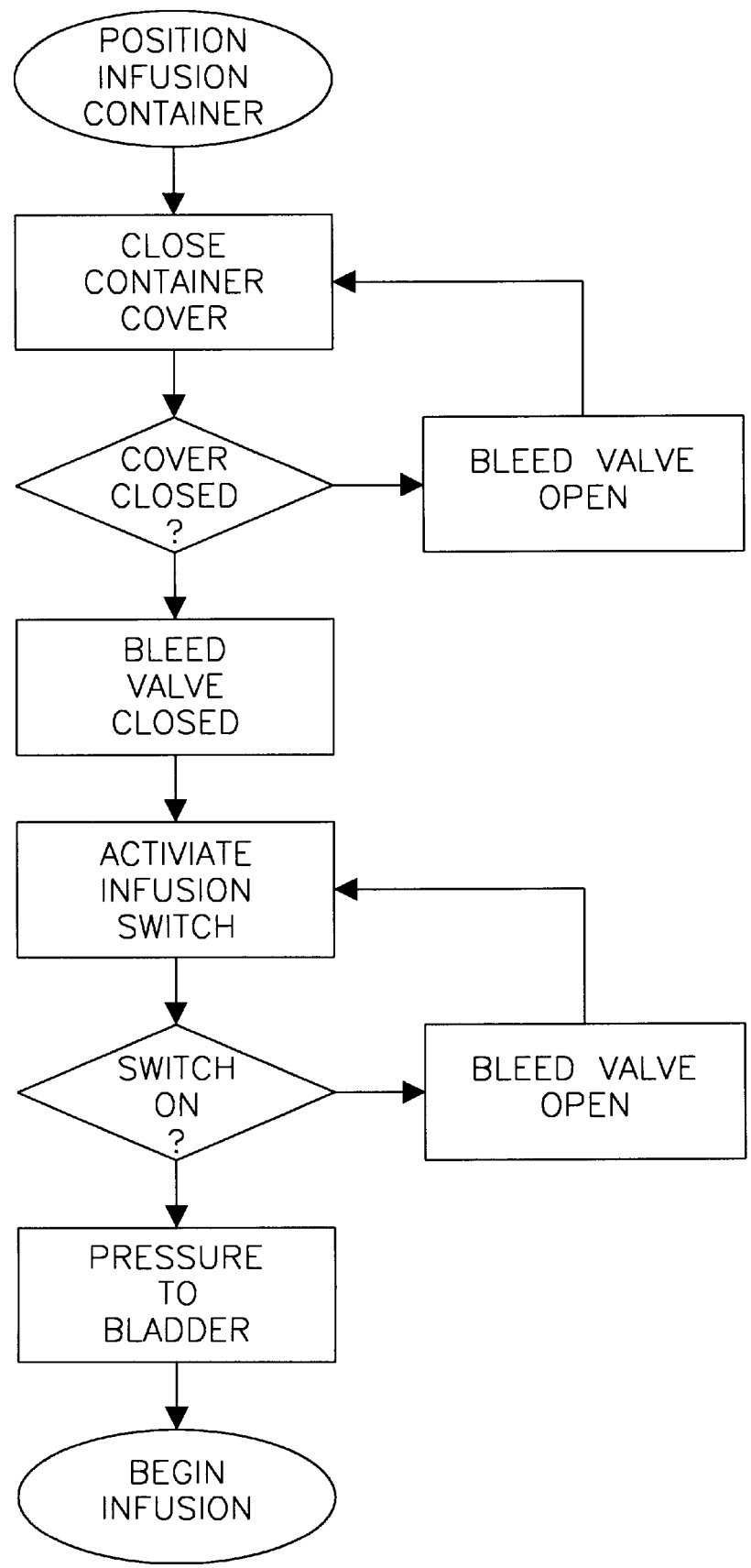
FIG. 7 is a simplified flow diagram illustrating the operation of the safety switch, the door switch and the bleed valve in accordance with practice of the present invention.

An operational flow chart which depicts the sequence of operations necessary to perform an infusion in accordance with the invention is illustrated in FIG. 7. In particular, FIG. 7 depicts the functional sequencing of the interlock safety switch 42 and the on/off switch 38 and their importance to the safe operation of the pump.

As shown in FIG. 7, the infusion container is first positioned properly over the surface of the movable pressure plate 32. As the cover is closed over base, the interlock safety switch 42 is activated by being engaged by the cover. Were the cover not fully closed, the interlock safety switch would prevent pressurization of the bladder. The safety switch 42 is blocked from the pressurized $CO_2$ gas source and open to atmosphere in order to bleed any developed line pressure. When the cover is fully closed, the safety switch is open to the pressurized $CO_2$ gas source and closed to the atmosphere. In order to begin the infusion process, the on/off switch 38 must be operated in order to pressurize the bladder. If the switch 38 is off, the switch is closed to the gas source and open to atmosphere to bleed any line pressure. It is only when the switch 38 is on that the system is now open to the gas source for bladder pressurization. Thus, the on/off switch and the interlock safety switch function, in combination, to insure that infusion proceeds only when it is safe to do so.

A flow or pressure indicator 70 (best seen in FIGS. 1a–1d and FIG. 2) may be coupled to the bladder 30 and mounted in the housing in a manner such that a visual indication may be given that the system is pressurized and that there is sufficient pressure in the system to inflate the bladder. In the illustrated embodiment, the pressure indicator is a generally hollow cylinder holding a spring mounted pin which is coupled to the pressure system such that compressed $CO_2$ gas may enter the cylinder and push the pin outwardly from the cylinder against the pressure of the spring. In a well understood manner, the spring is selected to have a spring constant such that the spring load will be overcome only upon application of a force against the pin corresponding to at least the minimum pressure required for infusion. The cylinder is mounted such that it protrudes slightly through the front end piece (16 of FIGS. 1 and 2) of the housing and the pin may be formed of a material having a bright color so as to give a visual indication of system pressure when it is deployed.

Additional features of the infusion pump of the present invention include a clear plastic viewing lens 72 (best seen in FIGS. 1 and 2) provided in the top surface of the housing cover 12. The clear viewing lens 72 is positioned directly over the IV solution container and allows a patient to view the contents of the container during the infusion process. The clear viewing lens 72 allows a simple and effective determination of the amount of solution remaining in a solution container and also provides a means of determining whether the apparatus is functioning properly.

Two additional clear viewing ports 74 are provided on either side of the housing cover 12 and allow a user to observe the progression of the infusion by observing the rotational position of the back edge of the pivotally movable pressure plate 32. The location of the pressure plate 32 in the viewing ports or windows 74 can be directly correlated to the fill-state of the IV solution container. When the pressure plate is in the bottom of the window, the IV solution container is full, and when the pressure plate is in the top of the window the IV solution container is empty. Intermediate positions of the pressure plate within the window 74 give an indication of intermediate fill-states of the container. Thus, it will be understood that the pressure plate 32 in combination with the viewing ports or windows 74 suitably comprise an infusion progression gauge or a fill-state indicator.

Turning now to FIG. 6, an infusion set, indicated generally at 80, is provided and is adapted for use with the ambulatory infusion pump of the present invention. As illustrated in FIG. 6, the infusion set 80 suitably comprises clear, flexible, medical grade tubing 82, terminating at one end in a drug or bag spike 22, and at the other end in a conventional Luer-type medical connector 84. The infusion set 80 further comprises a check valve 86 to prevent "flashback" when, for example, the infusion pump is turned-off, the cover opened, and the system depressurizes. The infusion set 80 further comprises an air eliminating filter 88 of a type well understood in the art and a flow controlling resistive lumen or orifice 101, positioned immediately prior to the luer fitting 84. The characteristics of the flow controlling resistive lumen 101 may be selected to provide the proper flow rate of IV solution to be administered in a fashion well understood by those having skill in the art. Thus, accurate and controlled infusions may be provided with the infusion set 80 in combination with the ambulatory infusion pump of the present invention.

After each infusion therapy, disposable items such as the miniature $CO_2$ cylinder 26, the IV solution container, and the disposable infusion set 80 may be disposed of in a suitable manner. It should be noted that the miniature $CO_2$ cartridge 26 need not be disposed of after each infusion therapy, so long as there is sufficient gas remaining in the cylinder (i.e., sufficient pressure in the system) to power a next infusion. If it is determined, however, that there is insufficient $CO_2$ gas remaining in the cylinder, the cylinder is easily replaced by opening a trap-door (90 of FIG. 1d) in the bottom of the apparatus, unscrewing the $CO_2$ cylinder 26 from the bushing 34 and screwing a new $CO_2$ cartridge into place. It is also a feature of the embodiment of the present invention that a spare $CO_2$ cartridge can be affixed to the trap-door 90 in a compartment provided for such a purpose, such that it is readily accessible when the trap door is removed for a cartridge change.

An ambulatory infusion pump has been described that is simple, reusable, inexpensive to operate, and usable with standard manufacturers' IV solution containers to provide efficient, accurate and low cost infusion therapies. The ambulatory infusion pump of the illustrated embodiment uses a compact, reliable and cost effective energy source comprising miniature $CO_2$ gas cylinders of the type commonly used for life jackets and motorcycle tire inflation kits, for example. The reusable ambulatory infusion pump is particularly durable since it includes neither electronic components to control or monitor operation, nor batteries as a primary power source. Because of its compact and rugged construction the infusion pump according to the invention is able to function even after having been dropped, and because of its lack of electronics, the pump is able to operate even while submerged in water.

Various alternative embodiments of infusion pumps constructed in accordance with the invention will become immediately evident to one having skill in the art. In particular, although the ambulatory pump has been described as being powered by a miniature $CO_2$ cylinder configured to contain from about 8 to about 16 grams of $CO_2$ gas, the invention does not depend solely on $CO_2$ for its motive power. In particular, the same type of pressurized gas cylinder may container nitrogen ($N_2$), compressed air or any other suitable compressed gas which can be regulated to an operative pressure. Moreover, the cylinders themselves need not be restricted to the 8 to 16 gram range. Leland Ltd., Inc. of Bedminster, N.J., manufactures a variety of pressurized gas cylinders configured to contain from about 8 to about 80 grams of pressurized gas. The larger sizes of pressurized gas cylinders would be a particular benefit to the present invention in cases where the invention was being used in connection with a paramedical kit of the kind commonly carried by ambulances and the like. Often, paramedics are faced with situations in which trauma victims require multiple fluid infusions, each of relatively high volumes. Larger gas cylinders would, necessarily provide the additional motive power required to deliver these infusions without the fear of cylinder exhaustion at a critical moment.

While the ambulatory infusion pump of the present invention has been described in connection with a particular illustrated embodiment, it will be obvious to those having skill in the art that various changes and modifications to the construction and configuration of the various elements comprising the pump may be made without departing from the broad inventive scope thereof. It will be understood, therefore, that the invention is not limited to the particular embodiments or arrangements disclosed, but is rather intended to cover any changes, adaptations or modifications which are within the scope and spirit of the invention as defined by the appended claims.

I claim:

1. A portable, ambulatory infusion pump comprising:

a housing defining an interior volume, the housing having exterior dimensions so as to be held comfortably in a human hand, the housing further comprising;
 a base;
 a cover, configured to be slidably mounted on the base;
 an end portion, the end portion including an access opening communicating with the interior volume, the access opening configured to receive an infusion set access spike therethrough;
 a pressurization system, further comprising;
 a replaceable, miniature compressed gas cylinder;
 a mechanical pressure regulator coupled to the cylinder by a bushing;
 a flexible inflatable bladder connected to receive pressure-regulated gas, whereby the bladder is pressurized upon introduction of pressure-regulated gas and volumetrically expands in response thereto;
 a pressure member angularly disposed within the housing and having a substantially flat pressure surface;
 a pivotally movable pressure plate, the flexible inflatable bladder disposed between the pressure surface and the pivotally movable pressure plate, the bladder expansion causing the movable pressure plate to rotatable displace in response thereto, the pressure surface and rotatably movable pressure plate defining an area therebetween sized to accept a standard, disposable pre-filled infusion medicament container; and a safety interlock assembly, coupled between the pressure regulator and the inflatable bladder, the safety interlock assembly operatively responsive to the cover being completely mated to the housing base, the safety interlock assembly preventing introduction of the pressure-regulated gas to the bladder unless the cover is completely mated to the base.

2. The portable, ambulatory infusion pump according to claim 1, wherein the replaceable, miniature compressed gas cylinder is configured to contain from about 8 to about 20 grams of compressed gas at an internal cylinder pressure of from about 500 to about 1,000 psi.

3. The portable, ambulatory infusion pump according to claim 2, wherein the replaceable, miniature compressed gas cylinder is configured to contain about 16 grams of $CO_2$ gas at an internal at a nominal internal cylinder pressure of from about 800 to about 900 psi.

4. The portable, ambulatory infusion pump according to claim 3, wherein the mechanical pressure regulator is configured to regulate the cylinder pressure of the compressed gas and deliver the gas at a substantially constant outlet pressure in the range of from about 3 to about 25 psi to the flexible inflatable bladder.

5. The portable, ambulatory infusion pump according to claim 4, further comprising activation means for initiating an infusion, the activation means for preventing introduction of pressure-regulated gas to the bladder unless in an on condition, the activation means further for venting pressure-regulated gas from the bladder to the ambient atmosphere when in an off condition.

6. The portable, ambulatory infusion pump according to claim 5, wherein the activation means is a switch controlled two-way valve coupled between the mechanical pressure regulator and the safety interlock assembly.

7. The portable, ambulatory infusion pump according to claim 6, wherein the interlock safety assembly comprises a spring operated, piston controlled two-way valve, the valve including a protruding pin coupled to the piston, the pin engaged by an activation surface of the cover as the cover is slidably advanced to mate to the base.

8. A portable, ambulatory infusion system comprising:

a standard, disposable, flexible, pre-filled infusion medicament container including an outlet port adapted to be accessed by a standard infusion set port spike;
 a re-useable, mechanical infusion pump for receiving the medicament container and for infusing medicament into a patient in a rate controlled fashion, the pump including;
 a housing having exterior dimensions so as to enable the pump to be held comfortably in a human hand, the housing including an access opening configured to receive an infusion set port spike therethrough, the housing having a base, a cover and an end portion, in combination defining an interior volume;
 a mechanical pressure regulator disposed in the housing;
 a replaceable, miniature compressed gas cylinder coupled to the pressure regulator by a bushing, the regulator configured to provide gas at an outlet port at a substantially constant pressure;
 a pressure member angularly disposed within the housing and having a substantially flat pressure surface;
 a pivotably moveable pressure plate; and
 a flexible inflatable bladder disposed over the pressure surface and underlying the moveable pressure plate, the bladder connected to receive pressure-regulated gas, whereby the bladder is pressurized upon introduction of pressure-regulated gas and volumetrically expands, the bladder expansion causing the pivotably movable pressure plate to rotatably displace in response thereto;

wherein, the medicament container is disposed between the pivotably moveable pressure plate and the housing cover, the bladder expansion causing a substantially constant pressure to be applied to the container by squeezing the container between the moveable pressure plate and the cover to thereby infuse the medicament into a patient at a substantially constant rate.

9. The portable, ambulatory infusion system according to claim 8, further comprising an infusion set, coupled to the medicament container, the infusion set including;

clear, flexible tubing defining a flow path;

a port spike disposed at one end of the flow path, the spike configured to access a spike port of a standard infusion medicament container;

a check valve disposed along a flow path;

an air elimination filter; and a variable flow controlling resistive lumen, the lumen variably adjustable to define a selectable flow rate therethrough.

10. The portable, ambulatory infusion system according to claim 9, wherein the miniature compressed gas cylinder is configured to contain from about 8 to about 20 grams of compressed gas at an internal cylinder pressure of from about 500 to about 1,000 psi.

11. The portable, ambulatory infusion system according to claim 10, wherein the miniature compressed gas cylinder is configured to contain about 16 grams of compressed $CO_2$ gas at an internal cylinder pressure of from about 800 to about 900 psi.

12. The portable, ambulatory infusion system according to claim 11, wherein the mechanical pressure regulator is adapted to regulate the cylinder pressure of the compressed $CO_2$ gas and deliver the gas at a substantially constant outlet pressure in the range of from about 3 to about 25 psi.

13. The portable, ambulatory infusion system according to claim 12, further comprising:

activation means for initiating infusion, activation means for preventing introduction of pressure-regulated gas to the bladder unless in an on condition, the activation means further for venting pressure-regulated gas from the bladder to the ambient atmosphere when in an off condition; and a safety interlock assembly, coupled between the pressure regulator and the inflatable bladder, the safety interlock assembly operatively responsive to the cover being completely mated to the housing base, the safety interlock assembly preventing introduction of pressure-regulated gas to the bladder unless the cover is completely mated to the base.

14. The portable, ambulatory infusion system according to claim 13, wherein the cover includes a viewing port, overlying the medicament container, the viewing port providing visual access to the medicament container so as to allow a patient to view the progress of infusion.

15. The portable, ambulatory infusion system according to claim 14, further including a mechanical pressurization indicator coupled to the pressure regulator, the indicator operatively responsive to the regulator's outlet pressure, the indicator providing a pressurization indication so long as the regulator's outlet pressure exceeds a minimum bladder inflation pressure.

16. A portable, ambulatory infusion system comprising:

a standard, disposable, flexible, pre-filled infusion medicament container including an outlet port adapted to be accessed by a standard infusion set port spike;

a re-useable, mechanical infusion pump for receiving the medicament container and for infusing medicament into a patient in a rate controlled fashion, the pump including;

a housing having exterior dimensions so as to enable the pump to be held comfortably in a human hand, the housing including an access opening configured to receive an infusion set port spike therethrough, the housing having a base, a cover and an end portion, in combination defining an interior volume;

a mechanical pressure regulator disposed in the housing;

a replaceable, miniature compressed gas cylinder coupled to the pressure regulator by a bushing, the regulator configured to provide gas at an outlet port at a substantially constant pressure;

a pressure member disposed within the housing and having a substantially flat pressure surface;

a moveable pressure plate;

a flexible inflatable bladder disposed over the pressure surface and underlying the moveable pressure plate, the bladder connected to receive pressure-regulated gas, whereby the bladder is pressurized upon introduction of pressure-regulated gas and volumetrically expands, the bladder expansion causing the movable pressure plate to displace in response thereto; and a mechanical pressurization indicator coupled to the pressure regulator, the indicator providing a pressurization indication so long as the regulator's outlet pressure exceeds a minimum bladder inflation pressure, wherein the pressurization indicator is a spring-operated pin, the spring having a spring constant such that the spring force is overcome by a gas pressure, whereby the gas pressure forces the pin against the spring allowing the pin to protrude outwardly in a manner so as to be visible by a patient;

wherein, the medicament container is disposed between the moveable pressure plate and the housing cover, the bladder expansion causing a substantially constant pressure to be applied to the container by squeezing the container between the moveable pressure plate and the cover to thereby infuse the medicament into a patient at a substantially constant rate.

17. The portable, ambulatory infusion system according to claim 16, wherein the cover includes fill state indicator means for gauging the progression of an infusion by indicating the volume capacity of an infusion container.

18. The portable, ambulatory infusion system according to claim 17, wherein the fill state indicator means comprises at least one clear viewing port disposed in the housing, the at least one viewing port positioned to allow observation of the rotational position of a back edge of the movable pressure plate.

19. The portable, ambulatory infusion system according to claim 18, wherein the housing includes spike capture means for securing the spike in the housing such that the spike cannot be inadvertently removed from the medicament container's spike port, once the medicament container and spike are placed within the infusion system housing.

* * * * *

UNITED STATES PATENT AND TRADEMARK OFFICE
CERTIFICATE OF CORRECTION

PATENT NO. : 5,954,696
DATED : September 21, 1999
INVENTOR(S) : Timothy C. Ryan

It is certified that error appears in the above-identified patent and that said Letters Patent is hereby corrected as shown below:

Column 11,
Line 63, change "rotatable" to -- rotatably --

Column 12,
Line 16, before "at a nominal" delete "at an internal".

Signed and Sealed this

Twenty-third Day of October, 2001

Attest:

*Nicholas P. Godici*

NICHOLAS P. GODICI
*Attesting Officer*   *Acting Director of the United States Patent and Trademark Office*